United States Patent

Reinhardt et al.

Patent Number: 5,770,737
Date of Patent: Jun. 23, 1998

[54] ASYMMETRICAL DYES WITH LARGE TWO-PHOTON ABSORPTION CROSS-SECTIONS

[75] Inventors: Bruce A. Reinhardt, Tipp City; Jayprakash C. Bhatt, Riverside; Lawrence L. Brott, Cincinnati; Stephen J. Clarson, Loveland, all of Ohio

[73] Assignee: The United States of America as represented by the Secretary of the Air Force, Washington, D.C.

[21] Appl. No.: 933,067

[22] Filed: Sep. 18, 1997

[51] Int. Cl.$^6$ ........................ C07D 409/10; C07D 213/02
[52] U.S. Cl. ........................................ 546/285; 546/280.4
[58] Field of Search .............................................. 546/285

[56] References Cited

PUBLICATIONS

Y. Ohmori, M. Uchida, C. Morishima, A. Fujii and K. Yoshino, "Enhancement of Emission Efficiency in Electroluminescent Diode Utilizing Vapor–Deposited Poly(alkylfluorene)", Jpn. J. Appl. Phys, vol. 32 (1993) Pt. 2, No. 11B, published Sep. 1993.

R. Dagani, "Devices Based on Electro–optic Polymers Begin to Enter Marketplace", C&EN, Mar. 6, 1996, pp. 22–27.

G. S. He, L. Yuan, N. Cheng, J. D. Bhawalkar, P. N. Prasad, L. L. Brott, S. J. Clarson and B. A. Reinhardt "Nonlinear optical properties of a new chromophore", J. Opt. Soc. Am. B, vol. 14, No. 5, published May 1997.

*Primary Examiner*—Alan L. Rotman
*Attorney, Agent, or Firm*—Charles E. Bricker; Thomas L. Kundert

[57] ABSTRACT

A two-photon absorbing chromophore of the formula

D—Ar—A wherein Ar is selected from the group consisting of

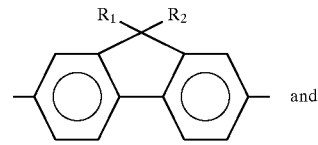
and

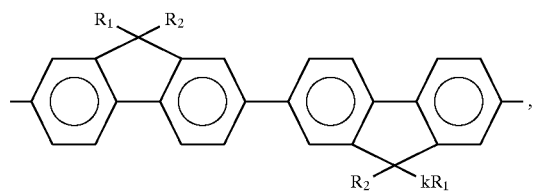

,

D is selected from the group consisting of

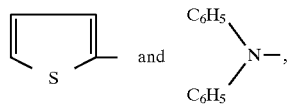

and A is selected from the group consisting of

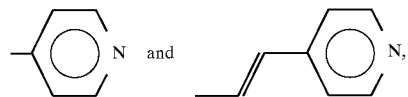

wherein $R_1$ and $R_2$ are alkyl groups having 8 to 12 carbon atoms, and wherein $R_1$ and $R_2$ are the same or different.

2 Claims, No Drawings

ASYMMETRICAL DYES WITH LARGE TWO-PHOTON ABSORPTION CROSS-SECTIONS

RIGHTS OF THE GOVERNMENT

The invention described herein may be manufactured and used by or for the Government of the United States for all governmental purposes without the payment of any royalty.

BACKGROUND OF THE INVENTION

In ordinary fluorescence microscopy, defocused images outside the depth of focus are superimposed on an image formed on the focal plane. This globally lowers the contrast of microscopic image, which makes determination of fluorescence intensity difficult.

Confocal microscopy offers several advantages over conventional microscopy. The shallow depth of field, generally about 0.5 to 1.5 µm, of confocal microscopes allows information to be collected from a well defined optical section rather than from most of the specimen as in conventional light microscopy. Consequently, out-of-focus fluorescence is virtually eliminated, which results in an increase in contrast, clarity and detection.

In a point scanning confocal system, the microscope lens focus the laser light on one point in the specimen at a time, i.e., the focal point. The laser moves rapidly from point to point to produce a scanned image. Very little of the laser light falls on other points in the focal plane. Both fluorescent and reflected light from the sample pass back through the microscope. The microscope and the optics of the scanner compartment focus the fluorescent light emitted from the focal point to a secont point, called the confocal point. A pinhole aperature, located at the confocal point, allows light from the focal point to pass through to a detector. Light emitted from outside the focal point is rejected by the aperature. Accordingly, only the image near the focal plane inside the sample is obtained as a microscopic image.

In two-photon absorption excitation type laser scanning fluorescence microscopy, a laser beam forms an optical spot having a high energy density and the optical spot three-dimensionally scans the inside of a sample in the same manner as in confocal laser scanning fluorescence microscopy. Because of the arrangement, fluorescence due to excitation based on two-photon absorption appears only from a point where the optical spot is located inside the sample but no fluorescence due to excitation based on two-photon absorption appears from other portions. Therefore, there appears no defocused image other than one on the focal plane, which improves the contrast of the microscopic image.

Two-photon excitation is made possible by the combination of (a) the very high, local, instantaneous intensity provided by the tight focusing available in a laser scanning microscope, wherein the laser can be focused to diffraction-limited waist of less than 1 micron in diameter, and (b) the temporal concentration of a pulsed laser.

A high intensity, long wavelength, monochromatic light source which is focusable to the diffraction limit such as a colliding-pulse, mode-locked dye laser, produces a stream of pulses, with each pulse having a duration of about 100 femtoseconds ($100 \times 10^{-15}$ seconds) at a repetition rate of about 80 MHz. These subpicosecond pulses are supplied to the microscope, for example by way of a dichroic mirror, and are directed through the microscope optics to a specimen, or target material, located at the object plane of the microscope. Because of the high instantaneous power provided by the very short duration intense pulses focused to the diffraction limit, there is an appreciable probability that a fluorophore (a fluorescent dye), contained in the target material, and normally excitable by a single high energy photon having a short wavelength, typically ultraviolet, will absorb two long wavelength photons from the laser source simultaneously. This absorption combines the energy of the two photons in the fluorophore molecule, thereby raising the fluorophore to its excited state. When the fluorophore returns to its normal state, it emits light, and this light then passes back through the microscope optics to a suitable detector.

The probability of absorption of two long wavelength photons from the laser source simultaneously is dependent upon the two-photon cross-section of the dye molecule.

Accordingly, it is an object of the present invention to provide chromophores having large two-photon cross-sections.

Other objects and advantages of the present invention will be apparent to those skilled in the art.

SUMMARY OF THE INVENTION

In accordance with the present invention there are provided asymmetrical fluorene-containing two-photon chromophores of the formula:

D—Ar—A wherein the Ar core is

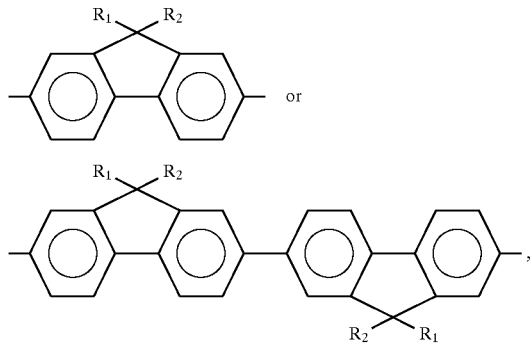

wherein $R_1$ and $R_2$ are alkyl groups having 8 to 12 carbon atoms, and wherein $R_1$ and $R_2$ are the same or different, wherein D is an electron donor moiety selected from the group consisting of

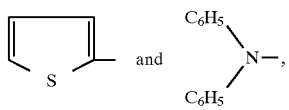

and wherein A is an electron acceptor moiety selected from the group consisting of

The following examples illustrate the invention:

EXAMPLE I

Preparation of 2.7-dibromo-9,9-di-n-decyl-9H-fluorene

Fluorene (27.70 g, 0.016 mol) and hexane (620 ml) were added to a three-necked round bottom flask equipped with a reflux condenser, a mechanical stirrer, and an addition funnel containing n-butyllithium (100 ml of a 2.0M solution in cyclohexane 0.2 mol). The fluorene was dissolved in hexane by stirring and warming the solution with a heat gun. When all the fluorene was in solution, the solution was allowed to cool to room temperature. The butyllithium solution was then added dropwise over a 45 min period at room temperature. The rust-colored solution was stirred an additional hour before adding N, N, N'N',-tetramethyleneethylenediamine (TME DA) (23.20 g, 0.2 mol) dropwise through a clean addition funnel. The solution was stirred an additional hour before 1-bromodecane (44.24 g, 0.2 mol) was added through another clean addition funnel. The pale orange solution was refluxed for 4 hours and then cooled to room temperature using an ice bath. A second equivalent of butyllithium (100.0 ml of a 2.0M solution in cyclohexane, 0.2 mol) was added at room temperature and was allowed to stir for an additional hour. Finally, 1-bromodecane (44.24 g, 0.2 mol) was added dropwise and the solution heated at reflux for an additional 6 hours.

The solution was cooled to room temperature and the resulting solid was vacuum filtered and the crystals rinsed with hexane. The solvent was removed under reduced pressure to yield a yellow oil that was purified by column chromatography on silica gel using hexane as the eluent. The product was futher purified by vacuum distillation (bp 257° C. (2 Torr)) to remove any excess bromodecane to afford 9,9-di-n-decyl-9H-fluorene as clear yellow oil in 93% yield. Mass Spec. m/z 446 ($M^+$), 418 ($M-C_2H_4$), 305 ($M-C_{10}H_{21}$). Elemental Analysis: Calculated for $C_{33}H_{50}$: C, 88.72; H, 11.28. Found: C, 88.47; H, 10.93.

A solution of 9,9-di-n-decyl-9H-fluorene (21.33 g, 0.047 mol), iodine (0.12 9, 0.47 mmol), and methylene chloride (170 ml) was stirred magnetically in a single-necked round bottom flask covered with aluminum foil to exclude light. Elemental bromine (5.18 ml, 0.10 mol) in methylene chloride (20 ml) was pipetted into an addition funnel which was then added dropwise to the reaction mixture over a period of 15 minutes. Residual bromine solution was rinsed out of the addition funnel into the reaction mixture using 20 ml of additional methylene chloride and the reaction was allowed to stir for 20 hours at room temperature. An aqueous solution (15% by weight) of sodium bisulfite ($NaHSO_3$) was then added to the reaction mixture and the resulting two phases allowed to stir for 30 min. The organic layer was then separated and washed 3 times with an equal volume of water and then dried over anhydrous magnesium sulfate. The solution was filtered, concentrated and the resulting solid recrystallized from absolute ethanol to yield 2,7-dibromo 9,9-di-n-decyl-9H-fluorene as white crystals, mp 38.1° C.–38.4° C. in 82.8% yield. Mass Spec. m/z 602, 604, 606 ($M^+$), 461, 463, 465 ($M-C_{10}H_{21}$), 382, 384 (461-Br). Elemental Analysis: Calculated for $C_{33}H_{48}Br_2$: C, 65.56; H, 8.00; Br, 26.44. Found: C, 64.99; H, 8.21; Br, 27.25.

EXAMPLE II

Preparation of 4-(7-bromo-9,9-didecyl-9H-2-fluorenyl)pyridine 4-(tributylstannyl)pyridine (8.30 g, 22.56 mmol) was added directly to a single-necked round bottom flask equipped with a condenser and a magnetic stir bar that had been dried in an oven at 110° C. overnight. 2,7-dibromo-9,9-di-n-decyl-9F-fluorene (15.00 g, 24.81 mmol) was weighed into a beaker and dissolved in dry toluene (65 ml) which had previously degassed with nitrogen. The fluorene solution was pipetted into the round-bottom flask and the beaker rinsed with two 5 ml portions of degassed toluene. $Pd(PPh_3)_4$ (0.26, 0.22 mmol), $PdCl_2(PPh_3)_4$ (1.58 g, 2.25 mmol) and triphenylphosphine (1.30 g, 4.96 mmol) were added to the reaction flask and the solution heated at reflux until it turned black. The reaction mixture was cooled to room temperature, the toluene removed under reduced pressure and the residue disolved in hexane. The hexane solution was stirred vigorously with 100 ml of a 2% aqueous KF solution for 3 hours. The organic layer was separated, washed twice with equal volumes of water, dried over anhydrous $MgSO_4$, filtered and concentrated. The crude product was purified by column chromatography on silica gel using 85:15 hexane: THF solution. The purified compound was isolated in 58.5% yield as a light yellow oil. Mass Spec. m/z 601, 603, ($M^+$), 460, 462, ($M-C_{10}H_{21}$), 381 (460-Br). Elemental Analysis: Calculated for $C_{38}H_{52}NBr$: C, 75.72; H, 8.70; N, 2.32. Found: C, 69.01; H, 8.27; N, 1.46.

EXAMPLE III

Preparation of 4-(9.9-di-n-decyl-7-(2-thienyl)-9H-2-fluorenyl)pyridine 4-(7-bromo-9,9-didecyl-9H-2-fluorenyl)pyridine (2.32 g, 3.85 mmol) was weighed directly into a single-necked round bottom flask equipped with a magnetic stirrer and condenser which had been dried in an oven at 130° C. overnight. Toluene (20 ml, dried over $CaCl_2$ and freshly distilled) and 2-(tributylstannyl)thiophene (1.47 ml 4.62 mmol) were added to the flask and the solution was degassed with nitrogen for 15 min. Tetrakis(triphenylphosphine)palladium (0) (0.34 g, 0.29 mmol) was added and the solution was heated at reflux for 16 hr under nitrogen. The reaction was cooled to room temperature and the toluene was removed under reduced pressure. The product was isolated by column chromatography using silica gel and 90:10 hexane/THF as the eluent to afford a yellow oil in 72.38% yield. If the oil was allowed to stand at room temperature it slowly solidified into a pale yellow waxy solid mp 58° C.–61° C. Mass Spec. m/z 605, ($M^+$), 464, ($M-C_{10}H_{21}$). Elemental Analysis: Calculated for $C_{42}H_{55}NS$: C, 83.25; H, 9.15; N, 2.31. Found: C, 83.34; H, 8.89; N, 2.31.

EXAMPLE IV 2-(7-Bromo-9.9-di-n-decyl-9H-2-fluorenyl)thiophene 2-(tributylstannyl)thiophene (5.23 ml, 16.45 mmol) was added under nitrogen directly to a single-necked round bottom flask equipped with a condenser and a magnetic stir bar that had been previously dried in an oven overnight at 110° C. 2, 7,-dibromo-9,9-di-n-decyl-9H-fluorene (24.89 g, 41.17 mmol) was weighed into a beaker and dissolved in toluene (45 ml) which had been freshly distilled and degassed with nitrogen. The resulting fluorene solution solution was pipetted into the round-bottom flask and the beaker rinsed twice with 5 ml portions of degassed toluene. $PdCl_2(PPh_3)_2$ (0.58 g, 0.82 mmol) was added to the reaction flask and the solution heated at reflux until it turned black. The toluene was removed under reduced pressure and the residue dissolved in hexane. The hexane solution was stirred vigorously with 100 ml of a 2% solution of KF in water for 3 hours. The organic layer was separated, washed twice with an equal volume of water, dried over anhydrous $MgSO_4$, filtered and concentrated. The crude product was purified by column chromatography on silica gel using hexane as the eluent. The purified waxy solid (mp 36.9° C.–38.4° C.) was isolated in a 40.74% yield. Mass Spec. m/z 606, 608 (M+), 386, (M-Br-C$_{10}$H$_{21}$). Elemental Analysis: Calculated for C$_{37}$H$_{51}$BrS: C, 73.12; H, 8.46; Br, 13.15. Found: C, 72.42; H, 8.60; Br, 12.56

EXAMPLE V

Preparation of 2-(7-Tributylstannyl-9.9-di-n-decyl-9H-2-fluorenyl)thiophene 2-(7-Bromo-9,9-di-n-decyl-9H-2-fluorenyl)thiophene (9.00 g, 14.81 mmol) was weighed directly into an oven-dried single-necked round bottom flask equipped with a magnetic stirrer and condenser. The oil was dissolved in toluene (20 ml, dried over CaCl$_2$ and freshly distilled), after which bis(tributyltin) (22.45 ml, 44.42 mmol) was added. The solution was degassed with nitrogen for 15 minutes before the tetrakis(triphenylphosphine)-palladium(0) (0.17 g, 0.15 mmol) was added. The flask was then heated in an oil bath at 110° C. for 4 hours, after which time the reaction mixture turned black. The toluene was removed under reduced pressure and the residue redissolved in hexane. An aqueous solution of potassium fluoride (4.5 g in 200 ml of water) was added to the organic layer and vigorously stirred for 3 hours. The layers were separated and the hexane layer washed with 2 more times with equal volumes of water. The organic layer was separated, dried over anhydrous MgSO$_4$, filtered and concentrated. The product was purified by column chromatography on silica gel using 90:10 hexane/methylene chloride to yield 79.41% of a light brown oil.

Mass Spec. m/z 814, 816, 818 (M+), 757, 759, 761, (M-C$_4$H$_9$). Elemental Analysis: Calculated for C$_{49}$H$_{78}$SSn: C, 71.96; H, 9.61; S, 3.92. Found: C, 74.43; H, 10.40; S, 4.18.

EXAMPLE VI 7-(2-thienyl)-7'-(4-pyridyl)-9,9,9', 9'-tetra-n-decyl-2, 2'-bi-9H-fluorene 2-(7-tributylstannyl-9,9-di-n-decyl-9H-2-fluorenyl) thiophene (7.91 g, 9.67 mmol), 4-(7-bromo-9,9-di-n-decyl-9H-2-fluorenyl)pyridine (5.30 g, 8.79 mmol) and toluene (35 ml, dried over CaCl$_2$ and freshly distilled) were added to a single-necked round bottom flask equipped with a magnetic stirrer and condenser which had been dried in an oven at 110° C. overnight. The solution was degassed with nitrogen for 15 minutes before the tetrakis (triphenylphosphine)palladium(0) catalyst (1.52 g, 1.32 mmol) was added. The mixture was heated for 16 hours at reflux under nitrogen. The toluene was removed under reduced pressure and the residue was redissolved in hexane and the solution filtered through a thick pad of Celite 545. The filtrate was then stirred vigorously with 200 ml of a 1% solution of potassium fluoride in water. The organic layer was separated and washed twice more with equal parts of water. The hexane was dried over anhydrous MgSO$_4$ filtered and concentrated. The product was purified by column chromatography using silica gel which had been activated in an oven at 80° C. for 24 hours. The column was eluted with 90:10 hexane:ethylacetate to afford a yellow oil in 73.68% yield. When the oil was allowed to stand for several days at room temperature in solidified into a pale yellow waxy solid mp 59° C.–61.5° C. Elemental Analysis: Calculated for C$_{75}$H$_{103}$NS: C, 85.74; H, 9.88; N, 1.33. Found: C, 85.80; H, 10.18; N, 1.33.

EXAMPLE VII

Preparation of N,N-Diphenyl-7-bromo-9,9-di-n-decyl-9H-fluorene-2-amine

Diphenylamine (5.60 g, 33.09 mmol) and toluene (56 ml, dried over CaCl$_2$, distilled and degassed with nitrogen for 15 minutes) were added to a three-necked s round bottom flask equipped with a magnetic stir bar, thermometer, reflux condenser and an addition funnel containing n-butyllithium (20.8 ml of a 1.6M solution in hexanes, 33.28 mmol). The solution was cooled in a dry ice/acetone bath until the internal temperature was –5° C. The butyllithium was added dropwise so that the temperature never rose above 0° C. A white solid formed immediately. The reaction mixture was stirred at –5° C. for 90 minutes. While the reaction temperature was maintained at –5° C., tri-o-tolylphosphine (2.01 g, 6.60 mmol), 2,7-dibromo-9, 9-di-n-decyl-9H-fluorene (20,0 g, 33.08 mmol) and bis(dibenzylideneacetone)palladium(0) (0.33 9, 0.57 mmol) were added. The ice bath was removed and the mixture was heated in an oil bath for 72 hours at an internal temperature of 70° C. The toluene was then removed under reduced pressure. The product was purified by column chromatography using alumina and hexane to yield a light brown oil in 35.25%, yield. Mass Spec. m/z 691, 693 (M+). Elemental Analysis: Calculated for C$_{45}$H$_{58}$BrN: C, 78.01; H, 8.44; N, 2.02. Found: C, 79.32; H, 8.38; N, 1.51.

EXAMPLE VIII

Preparation of N.N-Diphenyl-7-(2-(4-pyridinyl) ethenyl)-9,9-di-n-decyl-9H-fluorene-2-amine N,N-diphenyl-7-bromo-9,9-di-n-decyl-9H-fluorene-2-amine (8.08 9,11.66 mmol), tri-o-tolylphosphine (1.42 g, 4.67 mmol), triethylamine (30 ml, degassed with nitrogen for 15 minutes), 4-vinylpyridine (2.52 ml, 23.32 mmol) and palladium(II) acetate (0.13 g, 0.58 mmol) were added to a single-necked round bottom flask equipped with a magnetic stirrer and reflux condenser. The solution was heated at reflux by means of an oil bath under nitrogen for 16 hours. The solvent was removed under reduced pressure and the residue dissolved in methylene chloride. The organic layer was washed 3 times with water, dried over anhydrous MgSO$_4$, filtered and concentrated. The product was purified by column chromatography using silica gel and 85:15 hexane:ethyl acetate to afford a yellow oil in 59.45% yield. The oil, upon standing for several days, gradually solidified to give a waxy solid (mp 88.4° C.–89.3° C.). Mass Spec. m/z 716 (M+), 576, (M-C$_{10}$H$_{20}$), 358 (M++). Elemental Analysis: Calculated for C$_{52}$H$_{64}$N$_2$: C, 87.10; H, 9.00; N, 3.90. Found: C, 87.17; H, 9.45; N, 3.35.

EXAMPLE IX

Determination of 2-Photon Absorption Cross-Section

The two photon absorption coefficients β and the molecular two-photon-cross-section $\sigma_2$ were determined from an experimental measurement of the transmitted intensity of a laser beam at 798 nm as a function of the incident intensity. According to the basic theoretical consideration, the two-photon absorption (TPA) induced decrease in transmissivity can be expressed as $$I(L) = I_O/(1 + I_O L \beta) \tag{1}$$

where I(L) is the transmitted beam intensity, $I_O$ the incident beam intensity, L the thickness of the sample, and β is the TPA coefficient of the sample medium. In the derivation of the above equation it is assumed that the linear attenuation of the medium can be neglected and the beam has a nearly uniform transverse intensity distribution within the medium. The TPA coefficient can be determined by measuring the transmitted intensity I(L) as a function of various incident intensities $I_O$ for a given medium with a given L value. The TPA coefficient β (in units of cm/GW) of a given sample is determined by $$\beta = \sigma_2 N_O = \sigma_2 N_A d_0 \times 10^{-3} \qquad (2)$$

$N_O$ is the molecular density of the material being measured (in units of 1/cm³), $\sigma_2$ the molecular TPA cross-section of the same material (in units of cm⁴/GW), $d_0$ is the concentration of the material (in units of M/L) and finally $N_A$, Avogadro's number. For known β and $d_0$, the value of $\sigma_2$ can be easily calculated from equation (2).

In practice, various optical detectors such as photodiodes, photomultipliers, photometers and optical power meters can be used to measure the incident beam intensity $I_O$ and the transmitted beam intensity I(L) separately. The change of the $I_O$ values can be done by using variable optical attenuators (such as neutral filters or rotatable polarizing prisms), or by varying the beam cross-section of the input laser beam (by changing the relative distance of the sample to the focal point of the input beam). The input laser beam used for the experimental measurements was a pulsed laser dye system with a wavelength of 800 nm, a spectral width of 1–10 nm, a pulse duration of 8–10 ns, a beam size (before focusing lens) of 3–5 nm, a beam divergency of 1.2–1.5 mrad, and a repetition rate between 1–30 Hz.

| Compound of Example | Concentration M/L | β cm/GW | $\sigma_2$ (×10⁻²⁰) cm⁴/GW | Solvent |
|---|---|---|---|---|
| III | 0.0935 | 0.295 | 0.525 | THF |
| VI | 0.0935 | 0.354 | 0.629 | THF |
| VIII | 0.0450 | 21 | 78 | THF |

These data clearly show increased size of the 2-photon cross-section as compared to most state-of-the-art organic compounds. The increased cross-section, when coupled with strong upconverted fluorescence, makes these chromophores more useful in fluorescent imaging application such as 2-photon laser scanning confocal microscopy where strong fluorescence is needed to obtain high resolution. Large 2-photon absorption cross-sections also lead to greatly improved optical limiting behavior. In addition the long chain alkyl groups incorporated into these materials lead to very high solubility in organic solvents and good compatibility with organic polymers. Solubility of these chromophores is generally at least 0.01 and up to about 35% in common organic solvents.

Two-photon absorbing dyes which exhibit upconverted fluorescence have also found use in other areas of photonic technology. These include 2-photon pumped upconverted lasing, 2-photon confocal microscopy, 2-photon photodynamic therapy, 2-photon optical power limiting, and 3D optical data storage.

Various modifications may be made in the instant invention without departing from the spirit and scope of the appended claims.

We claim:

1. A two-photon absorbing chromophore of the formula

D—Ar—A wherein Ar is selected from the group consisting of

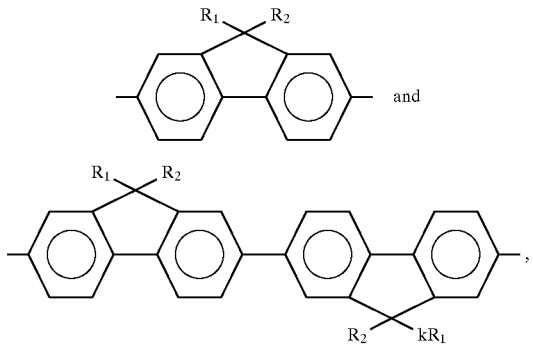

D is selected from the group consisting of

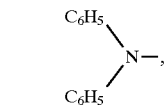

and A is selected from the group consisting of

wherein $R_1$ and $R_2$ are alkyl groups having 8 to 12 carbon atoms, and wherein $R_1$ and $R_2$ are the same or different.

2. The compound of claim 1 wherein Ar is

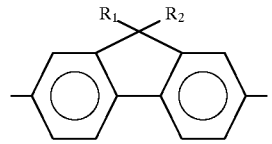

wherein $R_1$ and $R_2$ are n-decyl, D is

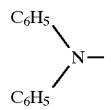

and A is

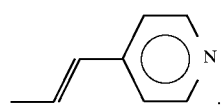

* * * * *